(12) United States Patent
Abboud et al.

(10) Patent No.: US 8,679,104 B2
(45) Date of Patent: Mar. 25, 2014

(54) WIDE AREA ABLATION OF MYOCARDIAL TISSUE

(75) Inventors: Marwan Abboud, Pierrefonds (CA); Fredric L. Milder, Galisteo, NM (US); George Klein, London (CA)

(73) Assignee: Medtronic Cryocath LP, Toronto, Ontario (CA)

( * ) Notice: Subject to any disclaimer, the term of this patent is extended or adjusted under 35 U.S.C. 154(b) by 1108 days.

(21) Appl. No.: 12/120,439

(22) Filed: May 14, 2008

(65) Prior Publication Data

US 2008/0215043 A1 Sep. 4, 2008

Related U.S. Application Data

(62) Division of application No. 11/119,399, filed on Apr. 29, 2005, now Pat. No. 7,794,455.

(51) Int. Cl.
*A61B 18/18* (2006.01)

(52) U.S. Cl.
USPC .............................................. 606/21; 606/22

(58) Field of Classification Search
USPC .................. 606/20–26; 607/104–106, 113
See application file for complete search history.

(56) References Cited

U.S. PATENT DOCUMENTS

| | | |
|---|---|---|
| 5,472,441 A | 12/1995 | Edwards et al. |
| 5,487,385 A | 1/1996 | Avitall |
| 5,575,766 A | 11/1996 | Swartz et al. |
| 5,584,803 A | 12/1996 | Stevens et al. |

(Continued)

FOREIGN PATENT DOCUMENTS

| | | |
|---|---|---|
| WO | 0007657 A1 | 2/2000 |
| WO | 0056237 A2 | 9/2000 |

(Continued)

OTHER PUBLICATIONS

Avitall, B., et al., New Cryotechnology for Electrical Isolation of the Pulmonary Veins, Journal of Cardiovascular Electrophysiology, Mar. 2003, pp. 281-286, vol. 14, No. 3.

*Primary Examiner* — Linda Dvorak
*Assistant Examiner* — Adam Avigan
(74) *Attorney, Agent, or Firm* — Christopher & Weisberg, P.A.

(57) ABSTRACT

The present invention advantageously provides a method and system for cryogenically ablating large areas of tissue within the left atrium. In an exemplary embodiment a cryotherapy device includes a catheter body having a substantially fixed diameter, a proximal end and a distal end; a first lumen for permitting passage of a cooling fluid from the proximal end to the distal end; a second lumen permitting return of the cooling fluid from the distal end to the proximal end; and an ablation element expandable from a first diameter that is substantially the same as the diameter of the catheter body to a second diameter that is at least twice the diameter of the catheter body, the ablation element having a surface portion that conforms to the uneven surface topography of the cardiac tissue. The ablation element can include one or more balloon and/or a flexible element that is deformed by moving the distal end of the catheter toward the proximal end of the catheter. The surface of the balloon can further be shaped by regulation of pressure within the one or more balloons. In an exemplary method a tissue ablation device is provided and tissue in the antrum of the left atrium is ablated with the device. In an exemplary method, only tissue in the antrum is ablated, and the ablation is created by freezing tissue.

20 Claims, 9 Drawing Sheets

(56) References Cited

U.S. PATENT DOCUMENTS

| | | | |
|---|---|---|---|
| 5,673,695 A | 10/1997 | McGee et al. | |
| 5,725,523 A | 3/1998 | Mueller | |
| 5,868,735 A | 2/1999 | Lafontaine | |
| 5,938,660 A | 8/1999 | Swartz et al. | |
| 5,964,778 A | 10/1999 | Fugoso et al. | |
| 5,971,979 A | 10/1999 | Joye et al. | |
| 5,980,486 A | 11/1999 | Enger | |
| 6,012,457 A | 1/2000 | Lesh | |
| 6,024,740 A | 2/2000 | Lesh et al. | |
| 6,036,697 A | 3/2000 | DiCaprio | |
| 6,106,518 A * | 8/2000 | Wittenberger et al. | 606/23 |
| 6,161,543 A | 12/2000 | Cox et al. | |
| 6,164,283 A * | 12/2000 | Lesh | 128/898 |
| 6,179,810 B1 | 1/2001 | Wantink et al. | |
| 6,179,827 B1 | 1/2001 | Davis et al. | |
| 6,214,002 B1 | 4/2001 | Fleischman et al. | |
| 6,233,491 B1 | 5/2001 | Kordis et al. | |
| 6,237,604 B1 | 5/2001 | Burnside et al. | |
| 6,241,754 B1 | 6/2001 | Swanson et al. | |
| 6,245,064 B1 | 6/2001 | Lesh et al. | |
| 6,254,599 B1 | 7/2001 | Lesh et al. | |
| 6,283,959 B1 | 9/2001 | Lalonde et al. | |
| 6,290,696 B1 | 9/2001 | Lafontaine | |
| 6,305,378 B1 | 10/2001 | Lesh | |
| 6,325,797 B1 | 12/2001 | Stewart et al. | |
| 6,355,029 B1 | 3/2002 | Joye et al. | |
| 6,387,092 B1 | 5/2002 | Burnside et al. | |
| 6,416,511 B1 | 7/2002 | Lesh et al. | |
| 6,432,102 B2 | 8/2002 | Joye et al. | |
| 6,471,694 B1 | 10/2002 | Kudaravalli et al. | |
| 6,502,576 B1 | 1/2003 | Lesh | |
| 6,514,245 B1 | 2/2003 | Williams et al. | |
| 6,514,249 B1 | 2/2003 | Maguire et al. | |
| 6,517,533 B1 | 2/2003 | Swaminathan | |
| 6,558,401 B1 | 5/2003 | Azizi | |
| 6,578,579 B2 | 6/2003 | Burnside et al. | |
| 6,585,733 B2 | 7/2003 | Wellman | |
| 6,595,988 B2 * | 7/2003 | Wittenberger et al. | 606/21 |
| 6,602,276 B2 | 8/2003 | Dobak, III et al. | |
| 6,641,511 B2 | 11/2003 | Patel et al. | |
| 6,645,234 B2 | 11/2003 | Evans et al. | |
| 6,648,878 B2 | 11/2003 | Lafontaine | |
| 6,648,879 B2 | 11/2003 | Joye et al. | |
| 6,648,883 B2 | 11/2003 | Francischelli et al. | |
| 6,652,515 B1 | 11/2003 | Maguire et al. | |
| 6,659,981 B2 | 12/2003 | Stewart et al. | |
| 6,666,858 B2 | 12/2003 | Lafontaine | |
| 6,685,732 B2 | 2/2004 | Kramer | |
| 6,689,128 B2 | 2/2004 | Sliwa, Jr. et al. | |
| 6,702,811 B2 | 3/2004 | Stewart et al. | |
| 6,740,104 B1 | 5/2004 | Solar et al. | |
| 6,755,822 B2 | 6/2004 | Reu et al. | |
| 6,758,847 B2 | 7/2004 | Maguire | |
| 6,875,209 B2 | 4/2005 | Zvuloni et al. | |
| 6,929,639 B2 | 8/2005 | Lafontaine | |
| 7,137,395 B2 | 11/2006 | Fried et al. | |
| 7,226,446 B1 | 6/2007 | Mody et al. | |
| 7,226,466 B2 | 6/2007 | Mody et al. | |
| 7,674,256 B2 * | 3/2010 | Marrouche et al. | 606/21 |
| 7,740,627 B2 | 6/2010 | Gammie et al. | |
| 2002/0087151 A1 | 7/2002 | Mody et al. | |
| 2002/0128636 A1 | 9/2002 | Chin et al. | |
| 2002/0183691 A1 | 12/2002 | Callister | |
| 2003/0125721 A1 | 7/2003 | Yon et al. | |
| 2003/0199861 A1 | 10/2003 | Lafontaine | |
| 2004/0034344 A1 | 2/2004 | Ryba | |
| 2004/0073203 A1 | 4/2004 | Yu et al. | |
| 2004/0073301 A1 | 4/2004 | Donlon et al. | |
| 2004/0225342 A1 | 11/2004 | Callister | |
| 2005/0020901 A1 | 1/2005 | Belson et al. | |
| 2005/0182395 A1 | 8/2005 | Lafontaine | |
| 2006/0271032 A1 | 11/2006 | Chin et al. | |

FOREIGN PATENT DOCUMENTS

| | | |
|---|---|---|
| WO | 0122897 A1 | 4/2001 |
| WO | 0200128 A2 | 1/2002 |
| WO | 0207628 A2 | 1/2002 |
| WO | 02083196 A2 | 10/2002 |
| WO | 03026719 A2 | 4/2003 |
| WO | 2005089853 A1 | 9/2005 |

* cited by examiner

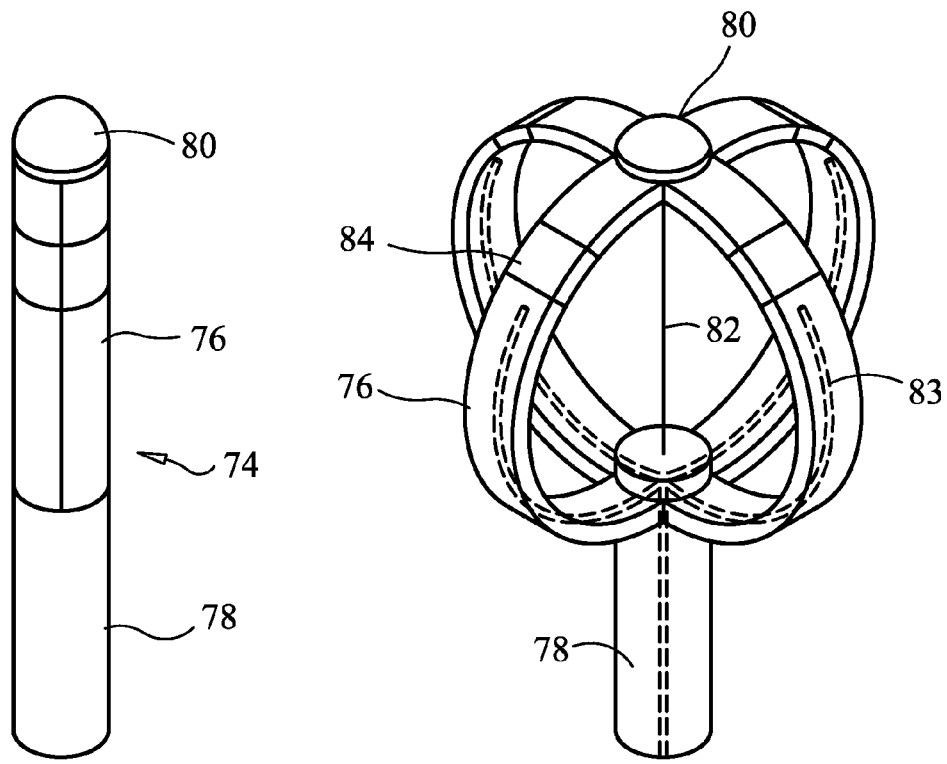
*Fig. 6*  *Fig. 7*
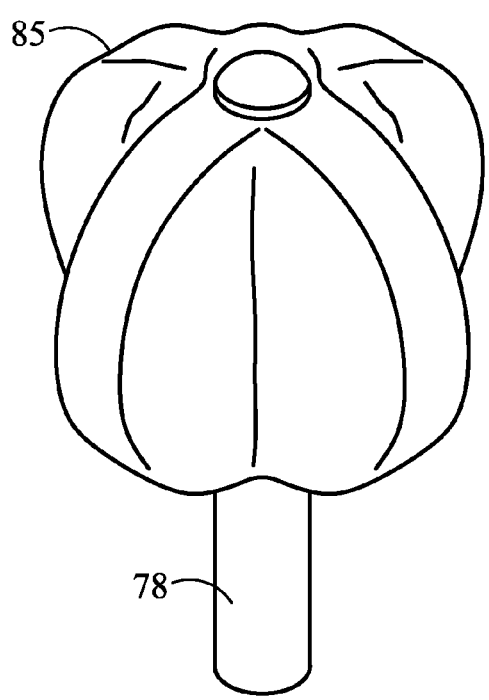
*Fig. 8*

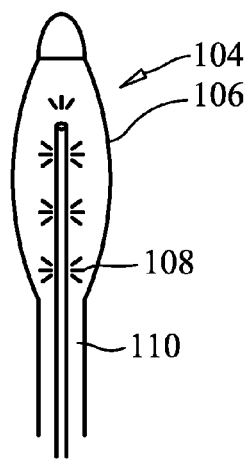
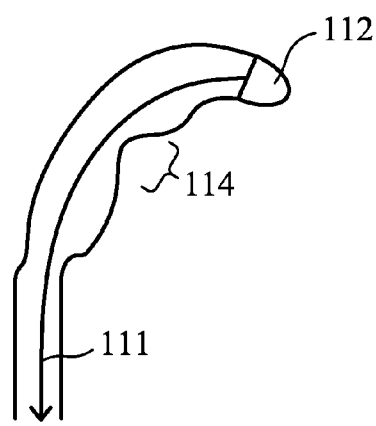
Fig. 12
Fig. 13
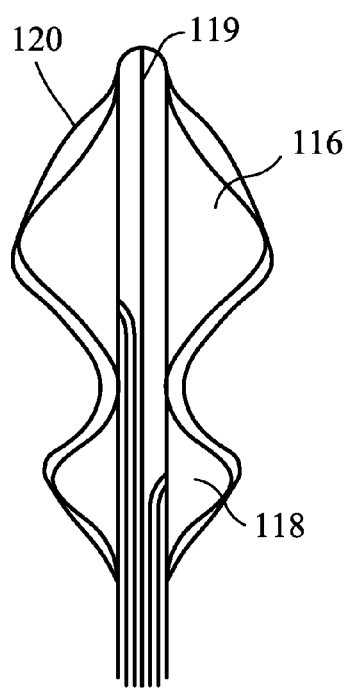
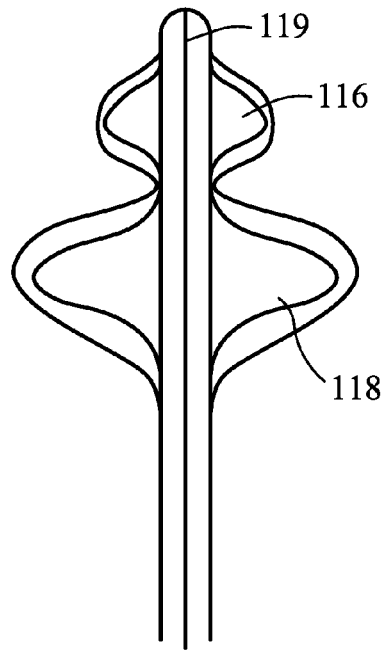
Fig. 14
Fig. 15

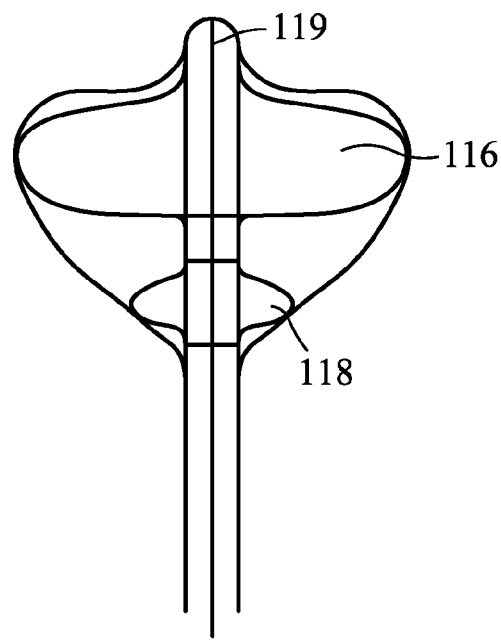 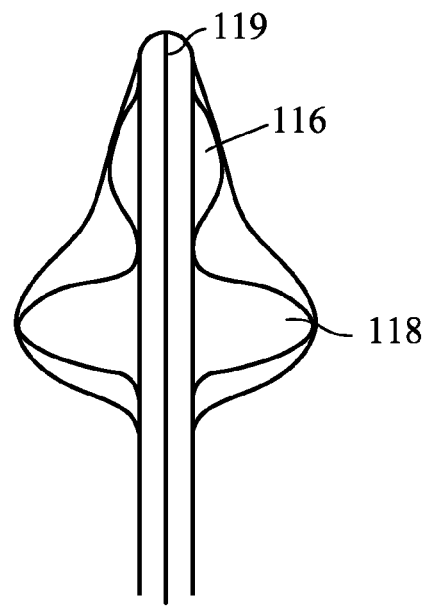
*Fig. 16*  *Fig. 17*
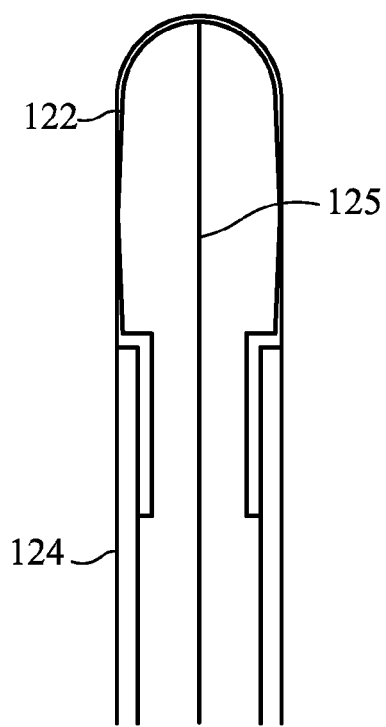 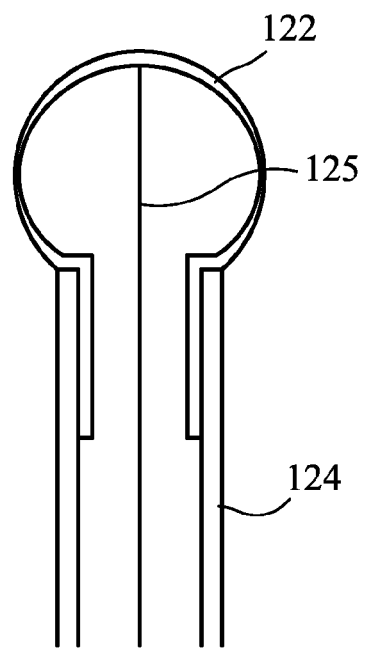
*Fig. 18*  *Fig. 19*

WIDE AREA ABLATION OF MYOCARDIAL TISSUE

CROSS-REFERENCE TO RELATED APPLICATION

This application is a divisional of U.S. patent application Ser. No. 11/119,399, filed Apr. 29, 2005, entitled WIDE AREA ABLATION OF MYOCARDIAL TISSUE, the entirety of which is incorporated herein by reference.

STATEMENT REGARDING FEDERALLY SPONSORED RESEARCH OR DEVELOPMENT n/a

FIELD OF THE INVENTION

The present invention relates to a method and system for interventional electrophysiology and minimally invasive cardiovascular surgery.

BACKGROUND OF THE INVENTION

Minimally invasive surgical techniques are known for performing medical procedures within all parts of the cardiovascular system. Exemplary known procedures include the steps of passing a small diameter, highly-flexible catheter through one or more blood vessels and into the heart. When positioned as desired, additional features of the catheter are used, in conjunction with associated equipment, to perform all or a portion of a medical treatment, such as vessel occlusion, tissue biopsy, or tissue ablation, among others. Almost always, these procedures are performed while the heart is beating and blood is flowing. Not surprisingly, even though visualization and positioning aids are adequate for general placement of the device, maintaining the device in a selected position and orientation can be difficult as the tissue moves and blood flows, especially during a procedure that must be done quickly. As diagnostic and visualization equipment and techniques have continued to evolve, it has become possible to identify tissue areas to be treated with greater precision than the ability to quickly situate the device and effectuate treatment.

In addition to the challenges presented by moving tissue and flowing blood, the actual topography of the tissue being treated presents challenges. For example, unlike stylized drawings that depict the interior of the chambers of the heart as having smooth, evenly curved walls leading neatly to tubular blood vessels, the interior surfaces of the heart's chambers are irregular, uneven, and fibrous, as are the openings to blood vessels. Thus, for procedures that call for uniform tissue contact or tissue contact along an extended line, the structure and techniques for use of known devices can be deficient in some regards.

Even if a device is capable of being properly placed and held in position at the proper orientation; and even if the device is suitable for the tissue topography at the treatment site, the device can be nevertheless not fully suitable to achieve the desired outcome. By way of example, catheter-based devices are known for placement in the left atrium for ablating tissue within the atrium for the purpose of electrically isolating one or more pulmonary veins from the atrium in an attempt to increase the success rate of atrial fibrillation ablation.

In one type of prior art device disclosed in U.S Patent Publication 2002/012836 A1, and as shown in FIG. 1 (prior art), a sheath or guide catheter 10 is inserted into a blood vessel 12 that leads to the right atrium 14 of the heart 16 and passed through an opening created in the septum 18 that separates the right and left atria into the left atrium 20. As shown in FIG. 2 (prior art), a treatment element 22 is passed through the guide catheter 10, deployed from an opening in the distal end thereof, and caused to form a substantially circular loop that is traverse or perpendicular to the longitudinal axis of the guide catheter 10. A distal tip element 24 that extends distally beyond the circular loop is inserted into a pulmonary vein 26 as a guide and placement aid for the loop. As shown in FIG. 3 (prior art), the treatment element 22 in the form of a loop is placed so that it encircles the opening or entry of the pulmonary vein 26, known as the ostium, and tissue is ablated by microwave heating of the contacted tissue. The intended result is a substantially uniform circle of ablated tissue 28 as shown in FIG. 4 (prior art). Also as shown in FIG. 4 (prior art), such a device can be used in an attempt to create linear lesions 30 and 32 as well.

In practice, uniform, unbroken lesion lines are hard to create with such loop shaped ablation elements. Also, with respect to both the circular and the linear lesions formed by microwave ablation, it should be noted that the lesion formed is relatively narrow and has a width that corresponds to about the width of the catheter. Devices that use a laser to ablate tissue provide a similar result; namely, a very narrow lesion. Further, because a laser ablates a very narrow line of tissue, precise alignment of the device is very important. However, for the reasons set forth above, such precision is very difficult to achieve.

In another type of device disclosed in U.S. Pat. No. 6,164,283 electrode elements, capable of ablating tissue when energized, are circumferentially disposed on the exterior of a balloon element that is placed at least partially within a pulmonary vein, so that the electrodes are positioned to form a circumferential conduction block along a circumferential region of tissue in a pulmonary vein wall. Other device configurations are disclosed that have an electrode band positioned on an expandable member for ablating a circumferential path around the ostium and tissue along the posterior atrial wall which surrounds the pulmonary vein.

Recently, companies such as CryoCath Technologies Inc., Montreal, Canada, have developed catheter based devices that cryogenically ablate tissue. These devices are structurally very different from RF catheter based devices, and they are not similar or comparable variations on the same theme. Not only are the structures that encompass the respective ablation technologies different, but so are the devices for controlling the ablation process, evaluating the progress and extent of ablation, and ensuring patient safety.

For example, to create a large "ring" with and RF catheter it is necessary to make a series of adjoining spot lesions of relatively small size using small electrode if one wishes to minimize RF output. This is significant because use of a large electrode and/or high power output can seriously injure tissue at other than the intended treatment site. This is especially important with respect to creating lesions in the pulmonary veins because the veins are juxtaposed with bronchial tubes and other sensitive pulmonary tissue within which it is highly undesirable to create ancillary lesions. By contrast, cryogenic ablation of tissues does not need to be accomplished "bit by bit" for fear to transmission of energy into tissue and the transfer of heat occurs at the medical device.

Another disadvantage common to RF and other non-cryogenic devices that was identified above is the difficulty of maintaining such a device in a selected position while the heart is beating. By contrast, a cryogenic device does not have this problem because the subfreezing temperatures created by the device causes the device to firmly stick or adhere to tissue at a treatment site. Still further, RF energy causes cellular death and side effects that are specific to the use of RF energy and that contrast considerably with the effects of cooling and the cellular death caused by freezing tissue.

Thus, although RF ablation may be appropriate and safe for tissue ablation in other areas of the body, clinical studies have revealed that creating of RF lesions in the pulmonary veins does not appear advantageous for the reasons set forth above. Further, RF ablation of the pulmonary veins has been associated with left atrial-esophageal fistula, pulmonary vein stenosis, tamponade, and significant radiation exposure. Therefore, if a cryogenic device were available as an alternative to RF ablation devices and techniques for the treatment of atrial fibrillation, it would be preferable to use the cryogenic device to avoid the problems created by the use of RF energy.

Notwithstanding the apparent advantages of cryoablation over other types of ablation, particularly RF, with respect to treatment of atrial fibrillation, very few cryoablation devices have been conceived for this purpose. Or, if cryoablation has been considered, it is mentioned as if it were synonymous with RF ablation, with no actual thought or disclosure provided that is enabling for such a structurally dissimilar device or that takes into account the very different effects of the use of the respective devices on tissue. For example, although U.S. Pat. No. 6,164,283 makes a brief, generalized reference to use of a cryoablation element to cool tissue, no specific details are set forth with respect to such a device.

Only one known device addresses issues related to cryoablation technology with respect to an attempted treatment of atrial fibrillation. Specifically, a cryoballoon catheter provided by Boston Scientific Corporation, Natick, Mass., has been used to create cryolesions by delivering liquid $N_2O$ into a semi-compliant balloon positioned at the pulmonary vein-left atrial interface. Thus, the device has basically been used as a substitute for an RF device to perform substantially the same procedure that is set forth in U.S. Pat. No. 6,164,283; namely, the creation of a substantially annular ring of ablated tissue at the ostium of the pulmonary vein. Although this device may obviate the adverse effects of the earlier RF devices, it would be desirable to provide a cryoablation device that more fully exploits the inherent advantages of a cryogenic ablation device.

SUMMARY OF THE INVENTION

The present invention advantageously provides a method and system for cryogenically ablating large areas of tissue within the left atrium.

In an exemplary embodiment a cryotherapy device is provided for modifying the electrophysiological properties of cardiac tissue having an uneven surface topography, wherein the device includes a catheter body having a substantially fixed diameter, a proximal end and a distal end; a first lumen for permitting passage of a cooling fluid from the proximal end to the distal end; a second lumen permitting return of the cooling fluid from the distal end to the proximal end; and an ablation element expandable from a first diameter that is substantially the same as the diameter of the catheter body to a second diameter that is at least twice the diameter of the catheter body, the ablation element having a surface portion that conforms to the uneven surface topography of the cardiac tissue. The ablation element can include one or more balloon and/or a flexible element that is deformed by moving the distal end of the catheter toward the proximal end of the catheter. The surface of the balloon can further be shaped by regulation of pressure within the one or more balloons.

The invention also include a method for modifying the electrophysiological properties of cardiac tissue wherein a tissue ablation device is provided and tissue in the antrum of the left atrium is ablated with the device. In an exemplary method, only tissue in the antrum is ablated, and the ablation is created by freezing tissue.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 6 is a side view of an exemplary ablation element for the system of FIG. 5;

FIG. 7 depicts the ablation element of FIG. 6 is an expanded state;

FIG. 8 shows an alternative embodiment of the ablation element of FIG. 6, wherein a membrane is disposed over expansion elements positioned in an expanded state;

FIG. 12 depicts the ablation element of FIG. 10 in a partially inflated state suitable for deflection;

FIG. 13 depicts the ablation element of FIG. 10 in the partially inflated state shown in FIG. 12 being deflected to a curved configuration;

FIG. 14 shows yet another embodiment of the ablation element;

FIGS. 15-17 illustrate the ablation element in exemplary deployment configurations;

FIG. 18 illustrates yet another embodiment of an ablation element;

FIG. 19 shows the ablation element of FIG. 18 in a deflected condition;

DETAILED DESCRIPTION OF THE INVENTION

With respect to the treatment of atrial fibrillation, it is believed that the creation of a conduction block or an interruption of the electrical signal flow path from the region of the atrium and the pulmonary vein is an effective treatment for atrial fibrillation. Further, while it is believed that the creation of a narrow annular lesion at or very near the ostium of the pulmonary vein is an effective way to create a conduction block, notwithstanding the difficulty of making such a lesion, it is believed that creating of one or more non-annular lesions in different locations is not only more readily accomplished with reliability but it is more clinically effective.

In view of the preceding, the present invention provides apparatus and methods for modifying the electrophysiological properties of large areas of tissue rather than narrow, annular lesions at locations that are not confined solely to the ostium, although ablation of tissue near the ostium and/or in the atrial wall may be included. More particularly, the present invention provides devices that are suitable to cryogenically ablate regions of tissue in the antrum region of the left atrium in addition to other atrial tissue that may be deemed to be arrhythmogenic. The antrum is the area between the mouth or ostium of a pulmonary vein and the atrium. The antrum of each pulmonary vein is not identical in size or shape and the tissue topography renders it very difficult or almost impossible to create a ring of tissue. Accordingly, the present method calls for ablating large regions of tissue in the antrum to render the tissue electrically dysfunctional.

Figure 1:
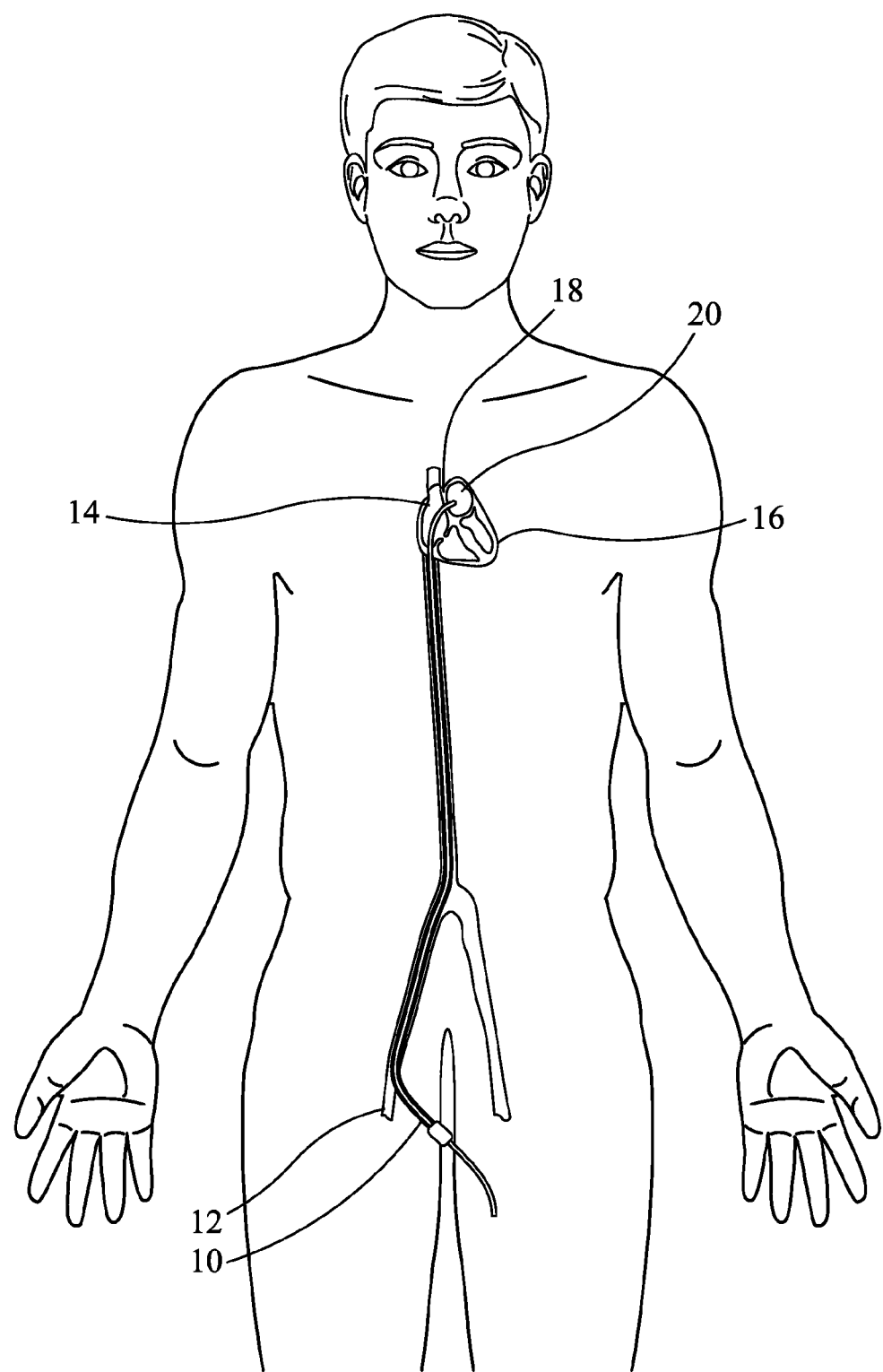
FIG. 1 depicts a prior art technique for placing a distal portion of a medical device within the heart.
Figure 3:
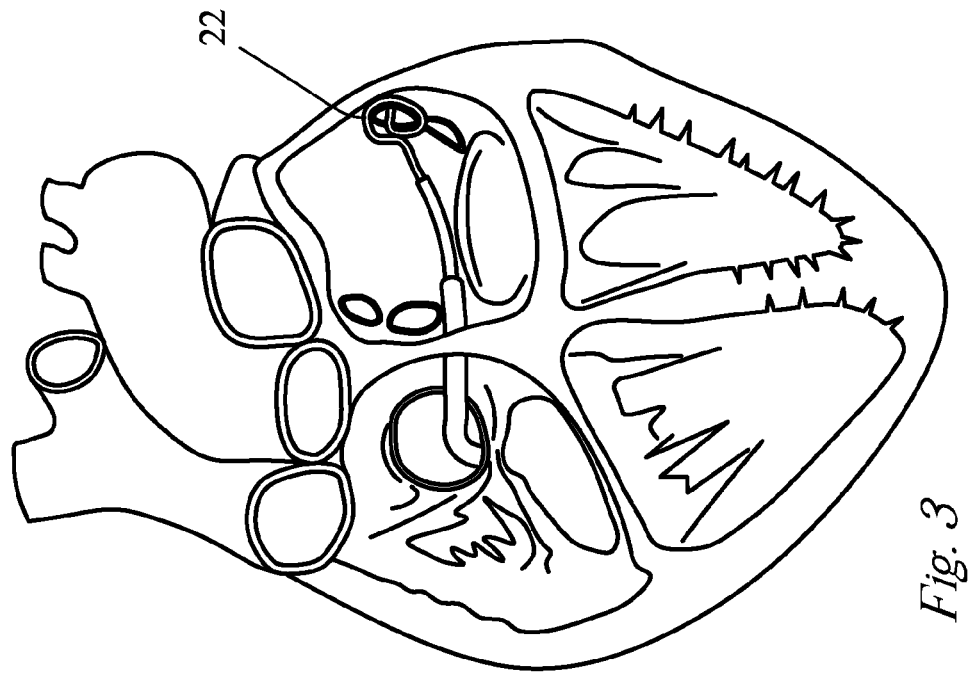
FIG. 3 depicts a prior art technique for creating a lesion with a prior art microwave ablation device.
Figure 2:
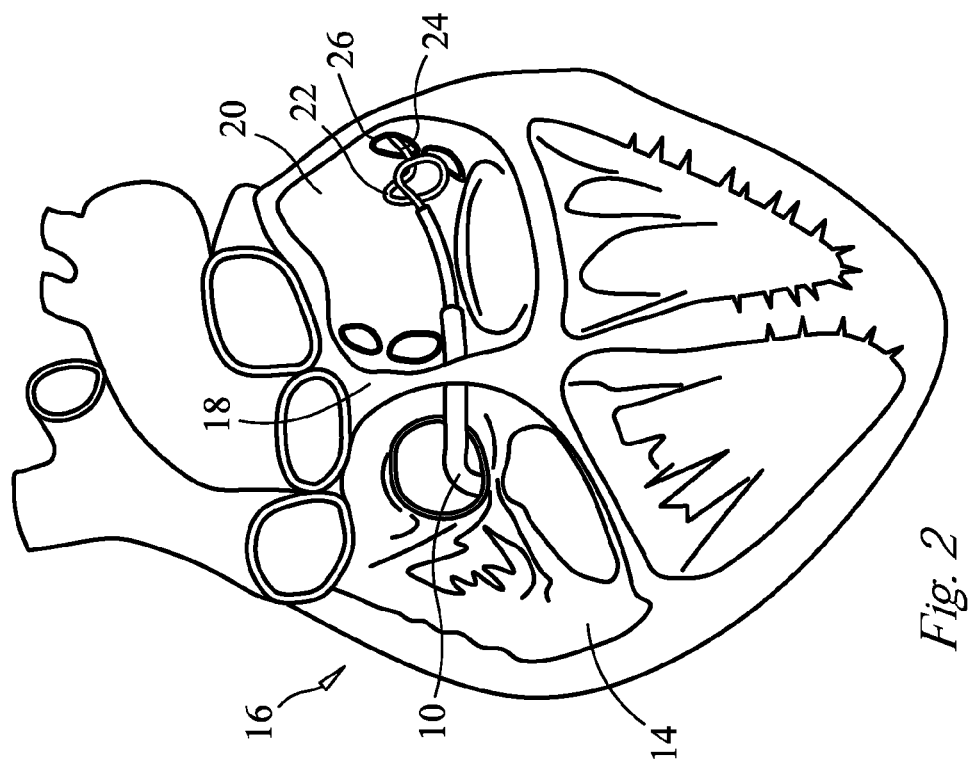
FIG. 2 illustrates a prior art technique for positioning a prior art device within the left atrium.
Figure 4:
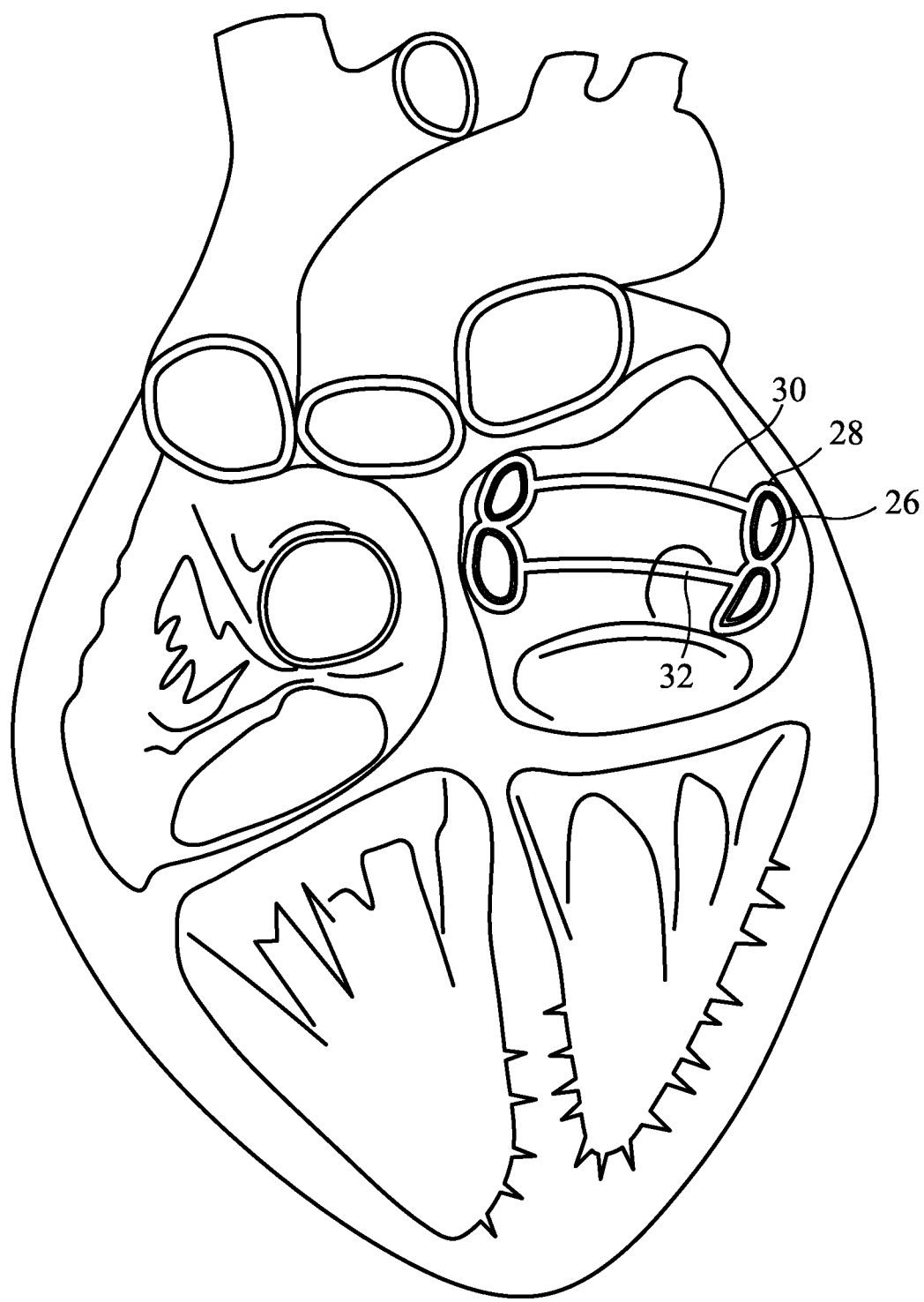
FIG. 4 shows lesions formed using the prior art techniques and devices of FIGS. 1, 2 and 3.
Figure 5:
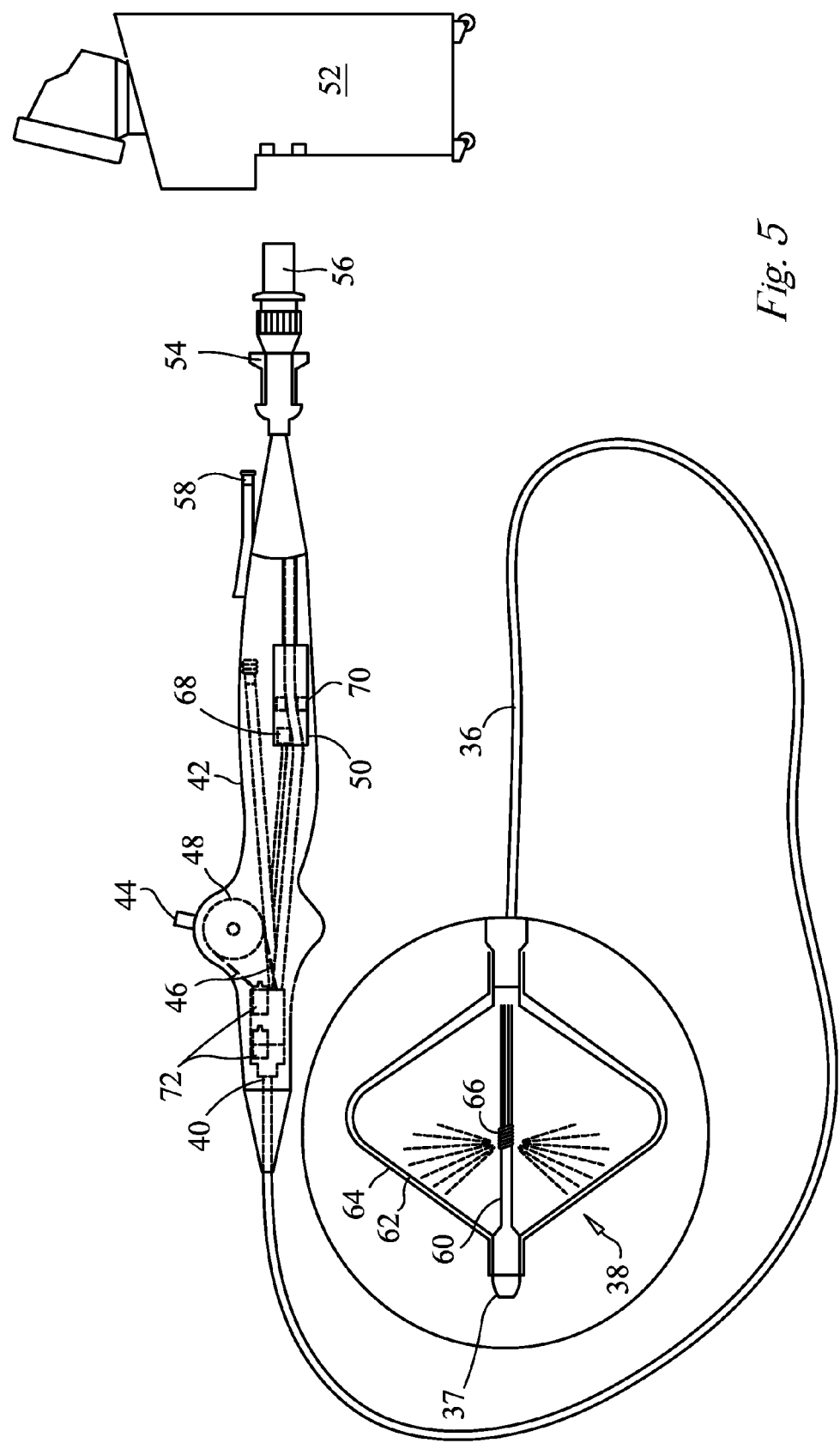
FIG. 5 is schematic illustration of a cryogenic ablation system in accordance with the present invention.

Referring now to FIG. 5, an exemplary system is depicted that is suitable for performing cryogenic antral ablation. The system includes an elongate, highly flexible ablation catheter 34 that is suitable for passage through the vasculature. The ablation catheter 34 includes a catheter body 36 having a distal end 37 with an ablation element 38 at or proximal to the distal end. The distal end 37 and the ablation element 38 are shown magnified and are described in greater detail below. The ablation catheter 34 has a proximal end 40 that is mated to a handle 42 that can include an element such as a lever 44 or knob for manipulating the catheter body 36 and the ablation element 38. In the exemplary embodiment, a pull wire 46 having a proximal end and a distal end has its distal end is anchored to the catheter at or near the distal end 37. The proximal end of the pull wire is anchored to an element such as a cam 48 in communication with and responsive to the lever 44. The handle 42 can further include circuitry 50 for identification and/or use in controlling of the ablation catheter or another component of the system.

Continuing to refer to FIG. 5, the handle 42 can also include connectors that are matable directly to a cryogenic fluid supply/exhaust and control unit or indirectly by way of one or more umbilicals. In the system illustrated, the handle 42 is provided with a first connector 54 that is matable with a co-axial fluid umbilical (not shown) and a second connector 56 that is matable with an electrical umbilical (not shown) that can further include an accessory box (not shown). In the exemplary system the fluid supply and exhaust, as well as various control mechanisms for the system are housed in a single console 52. In addition to providing an exhaust function for the ablation catheter fluid supply, the console can also recover and/or recirculate the cooling fluid. The handle 42 is provided with a fitting 58 for receiving a guide wire (not shown) that is passed into a guide wire lumen 60.

Still referring to FIG. 5, the ablation element 38 is shown as a double balloon, wherein an inner balloon 62 is contained by an outer balloon 64. A coolant supply tube 66 in fluid communication with the coolant supply in the console 52 is provided to release coolant from one or more openings in the tube within the inner balloon 62 in response to console commands and other control input. A vacuum pump in the console 52 creates a low pressure environment in one or more lumens within the catheter body 36 so that coolant is drawn into the lumen(s), away from the inner balloon, and toward the proximal end of the catheter body. The vacuum pump is also in fluid communication with the interface of the inner and the outer balloons so that any fluid that leaks from the inner balloon is contained and aspirated. Still referring to FIG. 5, the handle includes one or more pressure sensors 68 to monitor the fluid pressure within one or both of the balloons, blood detection devices 70 and pressure relief valves 72. When coolant is released into the inner balloon 62, the inner and the outer balloon 64 expand to a predetermined shape to present an ablation surface, wherein the temperature of the ablation surface is determined by the material properties of the specific coolant selected for use, such as nitrous oxide, along with the pressure within the inner balloon and the coolant flow rate.

Although the double balloon type ablation element 38 illustrated in FIG. 5 can be an effective ablation tool, FIGS. 6-20 illustrate other configurations for the ablation element that are capable of creating wide-area ablation patterns. For example, as shown in FIG. 6, a distal catheter portion 74 includes longitudinal elements 76 secured to a main catheter body 78 proximally, and to a tip element 80, distally. A pull wire 82 or pushrod connected to a manipulation element 44 at the proximal end of the catheter and to the tip element 80 is movable longitudinally to move the tip element longitudinally. Electrodes 84 can be associated with one or more of the longitudinal elements for use in monitoring or evaluating electrical activity in tissue.

As shown in FIG. 7, the pull wire 82 has been pulled proximally to draw the tip element 80 toward the catheter body 78. This causes the longitudinal elements 76 to deform and bend or bow radially outward. In one embodiment, each of the longitudinal elements 76 are provided with coolant injection tubes 83 disposed within a lumen defined by each longitudinal element, wherein coolant is recovered in the lumen which is in fluid communication with a low pressure source. Thus, each of the longitudinal elements 76 are cooled. Although the injection tubes 83 can all be supplied with coolant simultaneously, if desired, less than all of the injection tubes can be supplied with coolant to provide selectively radial cooling.

As shown in FIG. 8, the longitudinal elements can support a single or a double layer flexible member 85 that envelops them. Instead of, or in addition to coolant being circulated through the longitudinal members as discussed with respect to FIG. 7, coolant can be circulated through the chamber defined by the elements and the flexible member as described with respect to FIG. 5 and the pull wire 82 can be used to deform the balloon by moving the distal end of the device proximally and distally.

Figure 9:
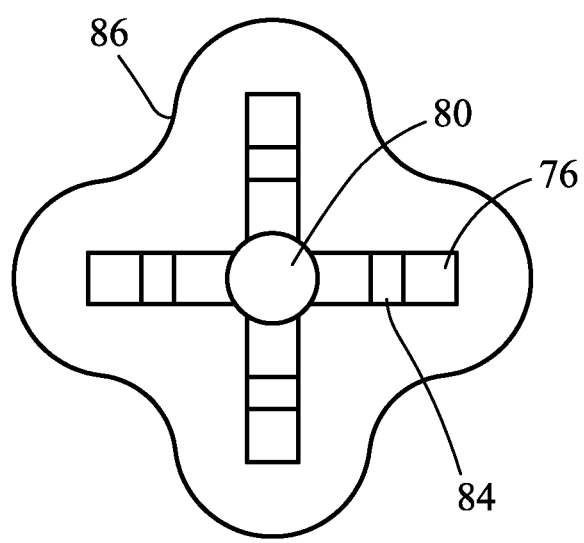
FIG. 9 is a front view of the ablation element of FIG. 6, wherein an ablation pattern created by the device is shown.

FIG. 9 is a front view of the device of FIGS. 7 and 8 and it illustrates the general shape of the periphery 86 of a lesion formed by cryoablation using the exemplary device in the expanded state. By contrast, spot or linear lesions can be created when the distal catheter portion 74 is in the non-expanded state illustrated in FIG. 6.

Figure 10:
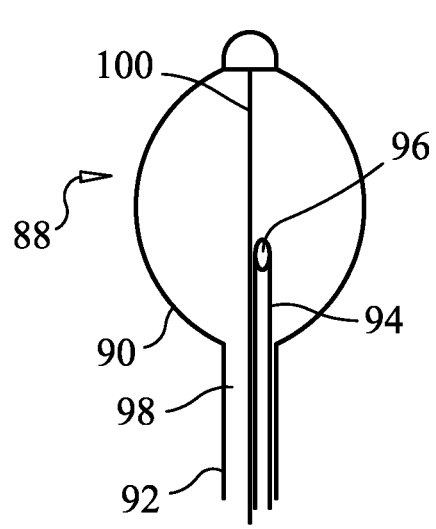
FIG. 10 illustrates an alternative embodiment for the ablation element in a partially expanded state.
Figure 11:
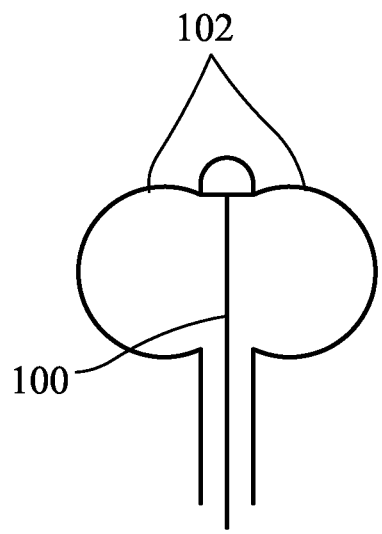
FIG. 11 illustrates the ablation element of FIG. 10 in a fully expanded state.

Referring now to FIG. 10, a catheter is provided with an ablation element 88 similar to the double balloon structure of FIG. 5 so that a distal tip region 90 is radially expandable to at least double the diameter of a catheter body 92 over a 2 cm to 3 cm length. The ablation element 88 is provided with a cryogenic fluid injection tube 94 having one or more fluid outlets 96 along its length in the distal tip region. Coolant is withdrawn though an outer lumen 98 at reduced pressure. A pull wire 100 or pushrod is used to deflect the distal catheter portion as shown in FIG. 11 so that a large, distal facing surface 102 can be placed into contact with tissue. Although the balloon when inflated as shown in FIG. 10 has a substantially greater radius than the catheter body 92, when the pull wire 100 is used to draw the distal tip toward the catheter body as shown in FIG. 11, the balloon expands even further and presents a flattened tip that is suitable to blot large areas of tissue.

Referring now to FIG. 12, an ablation element 104 is provided with a distal portion 106 that is inflatable, one or more coolant injection orifices 108 and an exhaust lumen 110. Referring to FIG. 13, the ablation element 104 is shown with a pull wire 111 or pushrod connected to a manipulation element at the proximal end of the catheter and the tip element 12 so as to be movable longitudinally to deflect the tip element off axis. In addition to providing a relatively long and wide ablation surface, the ablation element can be provided with a notch 114 to accommodate or fit over a ridge of tissue.

FIGS. 14-17 illustrate an embodiment for an ablation element, wherein first and second balloons, 116 and 118, respectively, are enveloped by a third balloon 120. The first and the second balloons 116 and 118 are in fluid communication with inflation and exhaust lumens as described above, wherein the third balloon 120 is only in communication with a vacuum or low pressure source. Each of the first and second balloons is provided with a shape and/or is pressurized to provide an overall surface topography for the ablation element. Additional shaping is provided by manipulation of a pull wire as described above or by regulation of the pressure in the exhaust flow path.

Referring now to FIGS. 18 and 19, yet another configuration for an ablation element is shown wherein an ablation element includes an elastically deformable, thermally-transmissive tip element 122 secured to the distal portion of a catheter body 124. When a load is applied to the tip element 122 it deforms. For example, FIG. 19 illustrates the tip element subject to an axial load, such as is encountered when the tip is pressed against tissue. As shown, the distal portion of the tip element 122 presents a wider ablation surface when deflected as compared to the non deflected state. When the load is removed from the tip, it returns to the shape illustrated in FIG. 18. Fluid supply and exhaust lumens are provided as disclosed above. Also as described above, a pull wire 125 can be secured to the tip element 122 to help deform the element so that it doesn't need to be pressed hard against tissue. In an exemplary embodiment the tip element 122 is configured so that it is biased into the shape illustrated in FIG. 18. Proximal tension is applied to the pull wire 125 to deform or aid in deforming the tip element to an expanded configuration as shown in FIG. 19. When proximally directed tension is reduced on the pull wire 125, the biasing force of the tip element causes it to return to the configuration shown in FIG. 18.

Figure 20:
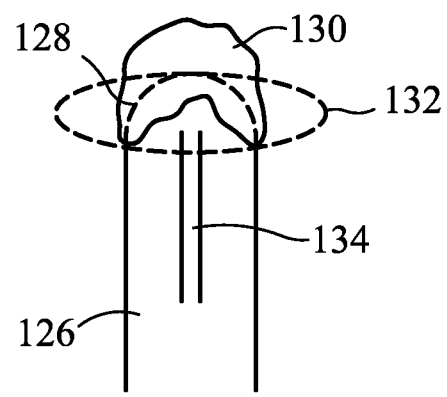
FIG. 20 show yet another ablation element in accordance with the invention.

FIG. 20 illustrates yet another configuration of an ablation element wherein a catheter body 126 has a distal end 128 covered with a mass of thermally conductive, highly elastic material, such as a cohesive gel 130. When the distal end 128 and the gel 130 are pressed against tissue, the gel deforms to provide an enlarged distal end portion as shown by the dashed line 132. Coolant exiting a coolant supply tube 134 cools the distal end 128 and the gel 130.

Figure 21:
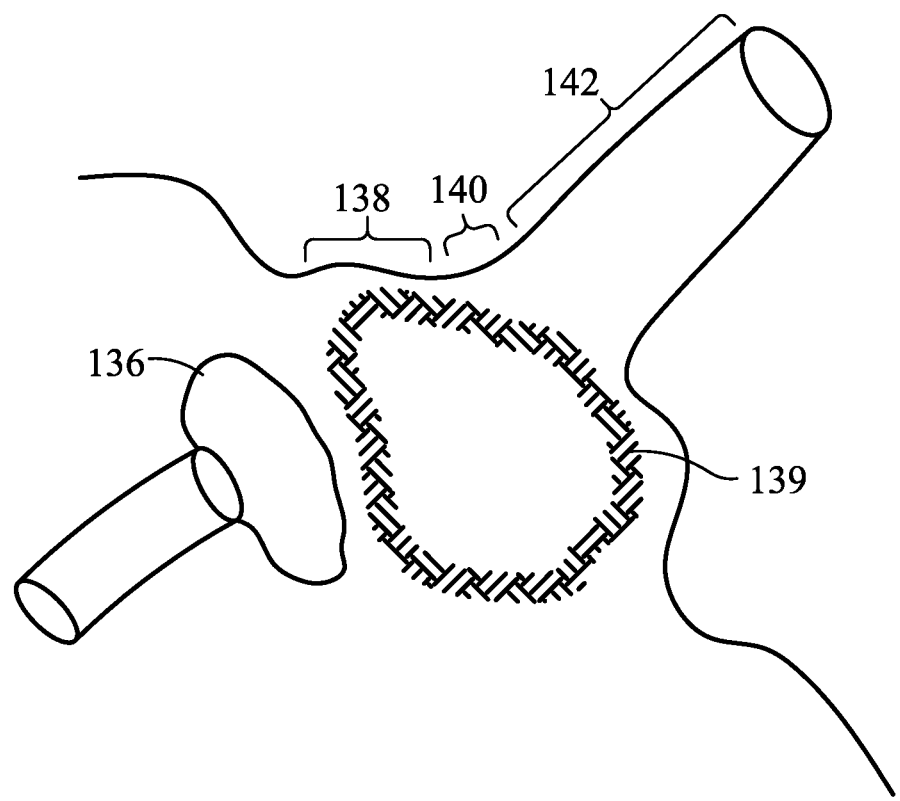
FIG. 21 illustrates an ablation device in accordance with the invention within the left atrium of the heart having created lesions in the left antral region.

Turning now to FIG. 21, an exemplary procedure is illustrated wherein an ablation element 136 in accordance with the invention has been delivered transeptally into the left atrium using known techniques. In the illustration, the ablation element 136 is a balloon that is partially inflated with a nitrous oxide coolant so that it has a "squishy" or highly compliant character and dimensioned so that it can "blot" or contact an area of tissue approximately 28 to 30 mm in diameter. In the exemplary procedure, the balloon is inflated to the desired degree of firmness, or lack thereof, before being advanced toward tissue and the balloon's surface is chilled to a temperature in the range of minus 30 degrees Centigrade to minus 80 degrees Centigrade. The balloon is then placed into contact with tissue in the antrum 138 and the tissue is ablated. The balloon is moved to one or more additional areas of the antrum 138 until the desired tissue modification has been achieved. The balloon can be placed so as to created individual distinct lesions or overlapping lesions. In this fashion, large contiguous lesions can be created. The pattern 139 shown in FIG. 21 illustrates an exemplary lesion periphery created with the ablation element 136.

Because the doctor is not attempting to create a "ring," the balloon does not have to be centered on the ostium 140 and no anchoring is needed. In general, for any of the disclosed cryoablation devices, precise alignment is not as important as with respect to other devices. This is significant, because the precise positioning within the antrum is difficult to achieve. The balloon does not enter the pulmonary vein 142. However, depending upon placement of the balloon, the temperature achieved, and the duration that the balloon is left in place, is possible to ablate tissue in the ostium 140 in addition to tissue within the pulmonary vein 142, as well as the antrum 138.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method for modifying the electrophysiological properties of cardiac tissue comprising:
   providing a tissue ablation device having at least one balloon, a tip coupled to a distal portion of the balloon, a wire coupled to the tip, and a longitudinal axis;
   applying a force to the wire to manipulate a portion of the at least one balloon to define a distally facing surface that lies in a plane that is substantially orthogonal to the longitudinal axis of the tissue ablation device; and
   ablating tissue in the antrum of the left atrium by placing the distally facing surface in contact with the tissue and activating the device.

2. The method of claim 1, wherein ablating tissue is limited to only ablating tissue in the antrum.

3. The method of claim 1, wherein ablating tissue comprises freezing tissue of the antrum.

4. The method of claim 1, wherein ablating tissue includes ablating tissues in an ostium for a pulmonary vein.

5. The method of claim 4, wherein ablating tissue further includes ablating tissue in the pulmonary vein.

6. The method of claim 1, wherein ablating tissue includes creating two or more overlapping lesions.

7. The method of claim 1, wherein ablating tissue includes creating two or more substantially circular lesions, each lesion having a diameter greater than 10 mm.

8. The method of claim 1, wherein ablating tissue includes creating a contiguous lesion greater than 2 cm$^2$.

9. The method of claim 1, further comprising configuring the ablation device to have a first configuration that has a first surface area and a second configuration that has a second surface area, wherein the second surface area is at least twice the first surface area.

10. The method of claim 1, further comprising pliably conforming at least a portion of the ablation device to the tissue.

11. The method of claim 10, wherein the pliable conformation is accomplished at least in part by partially inflating the balloon of the ablation device.

12. The method of claim 1, further comprising configuring the first balloon into a first shape and configuring a second balloon into a second shape different from the first shape.

13. The method of claim 12, further comprising ablating tissue with both the first and second balloons.

14. The method of claim 13, wherein ablating tissue includes circulating a cryogenic fluid through at least one of the first and second balloons.

15. The method of claim 12, wherein configuring the first balloon into a first shape includes partially inflating the first balloon such that the first balloon is pliably conformable to the cardiac tissue.

16. The method of claim 15, wherein configuring the second balloon into a second shape includes partially inflating the second balloon such that the second balloon is pliably conformable to the cardiac tissue.

17. A method for modifying the electrophysiological properties of cardiac tissue comprising:
providing a tissue ablation device defining a longitudinal axis;
pliably conforming at least a portion of the ablation device to the tissue;
manipulating a portion of the ablation device to define a distally facing tip by pulling on a portion of the ablation device, the distally facing tip lying in a plane that is substantially orthogonal to the longitudinal axis of the tissue ablation device;
circulating a cryogenic fluid through at least a portion of the tissue ablation device; and
ablating tissue in the antrum of the left atrium when the distally facing tip is in contact with the tissue.

18. The method of claim 17, wherein the pliable conformation is accomplished at least in part by partially inflating a balloon of the ablation device.

19. The method of claim 17, further comprising configuring a first balloon into a first shape and configuring a second balloon into a second shape different from the first shape, wherein configuring the first balloon into a first shape includes partially inflating the first balloon such that the first balloon is pliably conformable to the cardiac tissue.

20. The method of claim 19, wherein configuring the second balloon into a second shape includes partially inflating the second balloon such that the second balloon is pliably conformable to the cardiac tissue.

* * * * *